United States Patent [19]

Hartwig et al.

[11] Patent Number: 4,631,275
[45] Date of Patent: Dec. 23, 1986

[54] 1-OXADETHIACEPHALOSPORIN DERIVATIVES AND ANTIBACTERIAL USE THEREOF

[75] Inventors: Wolfgang Hartwig; Dieter Häbich; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 696,275

[22] Filed: Jan. 30, 1985

[30] Foreign Application Priority Data

Feb. 11, 1984 [DE] Fed. Rep. of Germany ....... 3404906

[51] Int. Cl.$^4$ .................... A01N 43/90; C07D 498/04
[52] U.S. Cl. ...................................... 514/210; 544/90
[58] Field of Search .......................... 544/90; 514/210

[56] References Cited

FOREIGN PATENT DOCUMENTS

| 0064740 | 11/1982 | European Pat. Off. . |
| 0074645 | 3/1983 | European Pat. Off. . |
| 0074653 | 3/1983 | European Pat. Off. . |
| 75805 | 4/1983 | European Pat. Off. . |
| 76463 | 4/1983 | European Pat. Off. . |
| 0088320 | 9/1983 | European Pat. Off. . |
| 3041160 | 5/1981 | Fed. Rep. of Germany . |

*Primary Examiner*—Richard L. Raymond
*Attorney, Agent, or Firm*—Sprung Horn Kramer & Woods

[57] ABSTRACT

1-Oxadethiacephalosporin derivatives of the formula

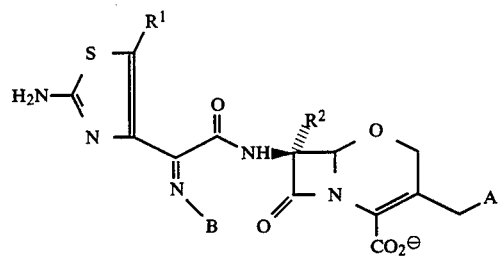

in which
$R^1$ denotes hydrogen or halogen,
$R^2$ denotes hydrogen or methoxy,
A is a nitrogen-containing positively charged N-containing heterocyclic 5-membered to 7-membered ring which in total can contain up to 4 heteroatoms from the group of N, O and S, to which ring up to two further rings can be fused and which ring may optionally be substituted, the ring being bonded via N,
B denotes optionally substituted alkoxy or amino, and the remaining radicals are more or less conventional, which are antibacterially active.

7 Claims, No Drawings

1-OXADETHIACEPHALOSPORIN DERIVATIVES AND ANTIBACTERIAL USE THEREOF

The invention provides novel 1-oxadethiacephalosporin derivatives which are substituted by particular ammonium radicals in the 3-position of the cephem ring.

These 1-oxadethiacephalosporin derivatives correspond to the general formula (1)

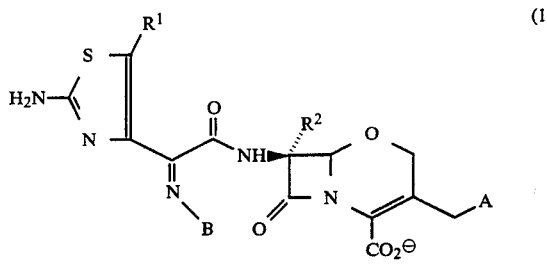

in which
$R^1$ denotes hydrogen or halogen, such as fluorine, chlorine or bromine,
$R^2$ denotes hydrogen or methoxy,
A is a nitrogen-containing positively charged radical bonded via N, in particular a heterocyclic 5-membered to 7-membered ring which in total can contain up to 4 heteroatoms from the group of N, O and S, to which ring up to two further rings can be fused and which ring may optionally be substituted,
B denotes an alkoxy group O—$R^3$,
in which $R^3$ represents $C_1$–$C_6$-alkyl or a —$(CH_2)_n(Z)_m R^4$ radical,
in which $R^4$ represents a $CO_2 R^5$ group
in which
$R^5$ denotes hydrogen, $C_1$–$C_4$-alkyl, $CH_2 O C_1$–$C_4$-alkyl or one equivalent of an alkali metal, alkaline earth metal, ammonium or an organic amine base, or denotes a nitrile group or carbamoyl group which can be monosubstituted or disubstituted at the nitrogen, and
n and m each denote 0 or 1, and
Z denotes an aryl radical or a

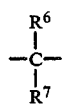

group,
wherein
$R^6$ and $R^7$ may be identical or different and denote hydrogen, aryl or a $C_1$–$C_4$-alkyl group, or
$R^6$ and $R^7$ together with the carbon to which they are bonded form a methylene or a $C_3$–$C_7$-cycloalkylidene group, alkyl and cycloalkyl moreover being optionally monosubstituted or polysubstituted.
In addition B represents

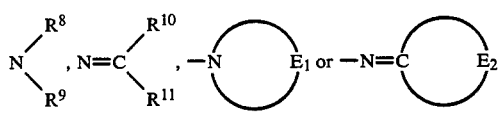

wherein
$E_1$ and $E_2$ independently of one another represent a doubly bonded organic radical and $R^8$, $R^9$, $R^{10}$ and $R^{11}$ independently of one another represent hydrogen or a radical such as alkyl, alkenyl, alkinyl, alkadienyl, cycloalkyl, cycloalkenyl, cycloalkadienyl, aryl or heterocyclyl, the radicals being optionally substituted or unsubstituted, or represent an acyl radical.

Preferred compounds are those
in which
$R^1$, $R^2$ and B have the above meaning and
A denotes a nitrogen-containing positively charged 5-membered or 6-membered ring containing up to a total of 3 nitrogen atoms and bonded via N, to which ring up to two further rings may be fused and which ring may optionally be substituted, unsubstituted and unsaturated.

Further preferred compounds are those
in which
$R^1$, $R^2$ and B have the above meaning and
A denotes a pyridinium radical

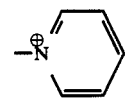

which is either unsubstituted or is monosubstituted or polysubstituted, preferably monosubstituted, disubstituted or trisubstituted (the substituents being identical or different) by substituted $C_1$–$C_6$-alkyl, by cyano-$C_1$–$C_3$-alkyl, epoxy-$C_2$–$C_6$-alkyl, trifluoromethyl or pentafluoroethyl, by hydroxyiminomethyl or $C_1$–$C_4$-alkoximinomethyl, by optionally substituted $C_2$–$C_6$-alkenyl, by $C_2$–$C_6$-alkinyl, by $C_3$–$C_7$-cycloalkyl or $C_3$–$C_7$-cycloalkylmethyl, the ring in both substituents being optionally substituted, by $C_4$–$C_7$-cycloalkenyl, by optionally substituted $C_1$–$C_6$-alkoxy, by epoxy-$C_2$–$C_6$-alkoxy, by $C_2$–$C_6$-alkenyloxy or $C_2$–$C_6$-alkinyloxy, by optionally substituted phenoxy or heteroaryloxy, by amino which may optionally be monosubstituted or disubstituted, by cyano, hydroxyl or mercapto, by $C_1$–$C_6$-alkylthio, $C_1$–$C_6$-alkylsulphinyl or $C_1$–$C_6$-alkylsulphonyl which are optionally substituted in the alkyl moiety, by methylthio, methylsulphinyl or methylsulphonyl which are optionally substituted in the methyl radical, by $C_2$–$C_6$-alkenylthio, $C_2$–$C_6$-alkenylsulphinyl or $C_2$–$C_6$-alkenylsulphonyl, by optionally substituted phenyl, benzyl or heteroaryl, by formyl or ketalised formyl, by optionally substituted $C_1$–$C_6$-alkylcarbonyl which can also be in the ketalised form, aryl-carbonyl, by $C_1$–$C_6$-alkylcarbonylamino, by carboxyl or $C_1$–$C_6$-alkoxycarbonyl or by sulphamoyl which may be monosubstituted at the nitrogen, to which pyridinium radical there may be fused one or two optionally substituted 3-membered to 7-membered rings which can each contain up to two heteroatoms and up to two double bonds and can also be aromatic or heteroaromatic.

The present invention is in particular directed to compounds
in which
$R^1$, $R^2$ and B have the above meaning and
A denotes a pyridinium radical

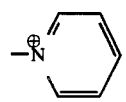

which is either unsubstituted or is monosubstituted or polysubstituted, preferably monosubstituted, disubstituted or trisubstituted, the substituents being identical or different, by $C_1$–$C_6$-alkyl which is monosubstituted or polysubstituted, by hydroxyl, carboxyl, $C_1$–$C_6$-alkoxycarbonyl, formyl or $C_1$–$C_6$-alkylcarbonyl, in which the carbonyl groups can also be in a ketalized form, carbamoyl, N-hydroxycarbamoyl, sulpho, $C_1$–$C_6$-alkyloxy, hydroxy-$C_1$–$C_6$-alkyloxy, $C_1$–$C_6$-alkylthio, $C_1$–$C_6$-alkylsulphinyl, $C_1$–$C_6$-alkylsulphonyl, $C_2$–$C_6$alkenyloxy, $C_2$–$C_6$-alkenylthio, $C_2$–$C_6$-alkenylsulphinyl or $C_2$–$C_6$-alkenylsulphonyl, by cyano-$C_1$–$C_3$-alkyl, epoxy-$C_2$–$C_6$-alkyl, hydroxyiminomethyl, $C_1$–$C_4$-alkoxyiminomethyl, trifluoromethyl or pentafluoroethyl, by $C_2$–$C_6$-alkenyl, which may be substituted by hydroxyl, by $C_2$–$C_6$-alkinyl, by $C_3$–$C_7$-cycloalkyl or by $C_3$–$C_7$-cycloalkylmethyl, the ring in both substituents also being optionally substituted by hydroxyl, halogen, carboxyl, $C_1$–$C_6$-alkoxycarbonyl or cyano, by $C_4$–$C_7$-cycloalkenyl, by $C_1$–$C_6$-alkoxy which can be substituted by hydroxyl, carboxyl or $C_1$–$C_6$-alkoxycarbonyl, by epoxy-$C_2$–$C_6$-alkoxy, by $C_2$–$C_6$-alkenyloxy or $C_2$–$C_6$-alkinyloxy, by optionally substituted phenoxy or heteroaryloxy, by amino which may be monosubstituted or disubstituted, the substituents being identical or different and being $C_1$–$C_6$-alkyl, formyl, $C_1$–$C_6$-alkylcarbonyl, $C_1$–$C_6$-alkoxycarbonyl, carbamoyl or $C_1$–$C_6$-alkylsulphonyl, by cyano, hydroxyl or mercapto, by $C_1$–$C_6$-alkylthio, $C_1$–$C_6$-alkylsulphinyl or $C_1$–$C_6$-alkylsulphonyl, which may be substituted by hydroxyl in the alkyl moiety, by methylthio, methylsulphinyl or methylsulphonyl which may be substituted in the methyl moiety by carboxyl or $C_1$–$C_6$-alkyloxycarbonyl, by $C_2$–$C_6$-alkenylthio, $C_2$–$C_6$-alkenylsulphinyl or $C_2$–$C_6$-alkenylsulphonyl, by phenyl, benzyl or heteroaryl which may also be substituted by halogen, by formyl or ketalized formyl, by $C_1$–$C_6$-alkylcarbonyl, which may also be substituted by hydroxyl and be in a ketalized form, by arylcarbonyl or $C_1$–$C_6$-alkylcarbonylamino, by carboxyl or $C_1$–$C_6$-alkoxycarbonyl or by sulphamoyl which may be optionally monosubstituted at the nitrogen by $C_1$–$C_6$-alkylaminocarbonyl, and to which pyridinium radical there may be fused an optionally substituted 3-7-membered, preferably 5-membered or 6-membered, ring which may contain up to two heteroatoms, preferably O, N or S, and up to two double bonds and may also be aromatic or heteroaromatic, and which may be monosubstituted or polysubstituted, but preferably monosubstituted, by the following substituents: by $C_1$–$C_6$-alkyl, $C_3$–$C_7$-cycloalkyl, $C_1$–$C_4$-alkoxy, $C_1$–$C_4$-hydroxyalkyl, halogen, hydroxyl, oxo, hydroximino, exomethylene, carboxyl, $C_1$–$C_6$-alkyloxycarbonyl, cyano, carbamoyl, sulphamoyl, amino, $C_1$–$C_4$-alkylamino or $C_1$–$C_4$-dialkylamino.

Very particularly preferred suitable compounds of the formula I are those in which $R^1$ and $R^2$ have the above meaning and A is a pyridinium radical which is either unsubstituted or monosubstituted, or polysubstituted, preferably monosubstituted, disubstituted, or trisubstituted, especially monosubstituted or disubstituted, for example by hydroxy-$C_1$–$C_4$-alkyl, such as especially hydroxymethyl, hydroxyethyl, hydroxypropyl, hydroxyisopropyl, hydroxybutyl, hydroxy-sec.-butyl or hydroxy-tert.-butyl, it also being possible, for example, for two or three hydroxyl groups to be present on the alkyl radical, by carboxy-$C_1$–$C_4$-alkyl, such as in particular carboxymethyl and carboxyethyl, by $C_1$–$C_4$-alkoxycarbonyl-$C_1$–$C_4$-alkyl, such as in particular methoxycarbonylmethyl, ethoxycarbonylmethyl, methoxycarbonylethyl, by $C_1$–$C_4$-alkylcarbonyl-$C_1$–$C_4$-alkyl, such as in particular methylcarbonylmethyl, ethylcarbonylmethyl, methylcarbonylethyl and ethylcarbonylethyl, the two alkyl groups of which may also be substituted by hydroxyl and the carbonyl group of which may also be present in a ketalized form, by carbamoylsubstituted $C_1$–$C_4$-alkyl, in particular carbamoylmethyl and carbamoylethyl, which may also be substituted by hydroxyl at the nitrogen, such as, in particular N-hydroxy-carbamoylmethyl, by sulpho-$C_1$–$C_4$-alkyl, such as in particular sulphoethyl or 1-hydroxy-1-sulphomethyl, by $C_1$–$C_4$-alkyloxy-$C_1$–$C_4$-alkyl, such as in particular methoxymethyl, ethoxymethyl, propoxymethyl, isopropoxymethyl, methoxyethyl, ethoxyethyl, methoxypropyl and methoxyisopropyl, which may also be substituted by hydroxyl, such as in particular hydroxyethoxymethyl and hydroxyethoxyethyl, by $C_1$–$C_4$-alkylthio-$C_1$–$C_4$-alkyl, such as in particular methylthiomethyl, ethylthiomethyl, methylthioethyl and ethylthioethyl, by $C_1$–$C_4$-alkylsulphinyl-$C_1$–$C_4$-alkyl, such as in particular methylsulphinylmethyl, ethylsulphinylmethyl, methylsulphinylethyl and ethylsulphinylmethyl, by $C_1$–$C_4$-alkylsulphonyl-$C_1$–$C_4$-alkyl, such as in particular methylsulphonylmethyl, ethylsulphonylmethyl, methylsulphonylethyl and ethylsulphonylethyl, by $C_3$-alkenyloxy-$C_1$–$C_4$-alkyl, such as in particular allyloxymethyl and allyloxyethyl, by $C_3$-alkenylthio-$C_1$–$C_4$-alkyl, such as in particular allylthiomethyl, by $C_3$-alkenylsulphinyl-$C_1$–$C_4$-alkyl, such as in particular allylsulphinylmethyl, by $C_3$-alkenylsulphonyl-$C_1$–$C_4$-alkyl, such as in particular allylsulphonylmethyl, by cyano-$C_1$–$C_3$-alkyl, such as in particular cyanomethyl and cyanoethyl, by epoxy-$C_2$–$C_3$-alkyl, such as in particular epoxyethyl and epoxypropyl, by trifluoromethyl, hydroximinomethyl and $C_1$–$C_3$-alkyloximinomethyl, such as in particular methoximinomethyl, by $C_3$–$C_4$-alkenyl, such as in particular allyl, 2-methylallyl and buten-3-yl which can also be substituted by hydroxyl, such as in particular hydroxyallyl and hydroxybutenyl, by $C_3$-alkinyl, such as in particular propargyl, by $C_3$–$C_6$-cycloalkyl and $C_3$–$C_6$-cycloalkylmethyl, such as in particular cyclopropyl, cyclobutyl, cyclopentyl, cyclohexyl and cyclopentylmethyl, the rings also being optionally substituted, for example by hydroxyl, such as in particular 1-hydroxy-1-cyclopentyl and 1-hydroxy-1-cyclohexyl, or by halogen, preferably chlorine, carboxyl, $C_1$–$C_4$-alkoxycarbonyl or cyano, by $C_5$–$C_6$-cycloalkenyl, such as in particular cyclo-pent-1-enyl and cyclohex-1-enyl, by $C_1$–$C_4$-alkoxy, such as in particular methoxy, ethoxy, propoxy, isopropoxy, butoxy, isobutoxy and tert.-butoxy, preferably methoxy, these alkoxy groups also optionally being substituted, for example by hydroxyl, carboxyl or $C_1$–$C_4$-alkoxycarbonyl, especially carboxymethoxy and methoxycarbonylmethoxy, by epoxy-$C_2$-$C_3$-alkoxy, such as in particular epoxyethoxy or epoxypropoxy, by $C_3$-alkenyloxy, such as in particular allyloxy, by $C_3$-alkinyloxy, such as in particular propargyloxy, by aryloxy, such as in particular phenoxy, by amino, by $C_1$-$C_5$-alkylamino, such as in particular ethylamino, by $C_1$-$C_5$-dialkylamino, such as in particular dimethylamino and diethoxyamino, by $C_1$-$C_4$-alkoxycarbonylamino, such as in particular methoxycarbonylamino and ethoxycarbonylamino, by $C_1$-$C_4$-alkylcarbonylamino, such as in particular methylcarbonylamino, by N-$C_1$-$C_4$-alkyl- and dialkyl-carbamoylamino, such as in particular N-methylcarbamoylamino and N,N-diethylcarbamoylamino, by $C_1$-$C_4$-alkylsulphonylamino, such as in particular methylsulphonyl- or ethylsulphonylamino, by cyano, by hydroxyl, in particular 3-hydroxy, by $C_1$-$C_4$-alkylthio, such as in particular methylthio, ethylthio, propylthio and isopropylthio, which may also be substituted by hydroxyl, in particular hydroxyethylthio, by $C_1$-$C_4$-alkylsulphinyl, such as in particular methylsulphinyl, ethylsulphinyl, propylsulphinyl and isopropylsulphinyl, which may also be substituted by hydroxyl, in particular hydroxyethylsulphinyl, by $C_1$-$C_4$-alkylsulphonyl, such as methyl-, ethyl-, propyl- or isopropyl-sulphonyl, which may also be substituted by hydroxyl, in particular hydroxyethylsulphonyl, by carboxymethylthio and $C_1$-$C_4$-alkoxycarbonylmethylthio, in particular methoxycarbonylmethylthio, by carboxymethyl-sulphinyl and -sulphonyl as well as $C_1$-$C_4$-alkoxycarbonylmethyl-sulphinyl and -sulphonyl, in particular methoxycarbonylmethyl-sulphinyl and -sulphonyl, by $C_3$-alkenylthio, such as allylthio and prop-1-ethylthio, by $C_3$-alkenylsulphinyl, such as allylsulphinyl and prop-1-enylsulphinyl, by $C_3$-alkenylsulphonyl, such as allylsulphonyl and prop-1-enylsulphonyl, by phenyl and benzyl, which may also be substituted, for example by halogen, especially chlorine, such as, for example, 4-chlorobenzyl, by 2'-thienyl and 3'-thienyl, by formyl and ketalized formyl, such as, for example, 1,3-dioxolan-2-yl, by $C_1$-$C_4$-alkylcarbonyl, especially acetyl and propionyl, preferably acetyl, which may also be hydroxy-substituted and be present in a ketalized form, such as, for example, 2-methyl-1,3-dioxolan-2-yl, by benzoyl, by $C_1$-$C_4$-alkylcarbonylamino, in particular acetylamino and propionylamino, by formylamino, by carboxyl, for example also 2,3,4-carboxyl, by $C_1$-$C_4$-alkoxycarbonyl, in particular methoxycarbonyl and ethoxycarbonyl, such as, for example, also 2,3,4-methoxycarbonyl or -ethoxycarbonyl, to which pyridinium radical there may also be fused an optionally substituted 5-membered or 6-membered ring which may contain up to two heteroatoms, preferably from the group of O, N and S, and up to two double bonds and which may also be aromatic or heteroaromatic (possible fused-on rings being in particular the following ring systems: cyclopenteno, dihydrocyclopenteno, cyclohexeno, dihydrocyclohexeno, benzo, furo, dihydrofuro, pyrano, dihydropyrano, thieno, dihydrothieno, thiopyrano, dihydrothiopyrano, pyrido, dihydropyrido, tetrahydropyrido, pyrimido, dihydropyrimido, tetrahydropyrimido, pyrazino, dihydropyrazino, tetrahydropyrazino, pyridazino, dihydropyridazino and tetrahydropyridazino, which may each be monosubstituted or polysubstituted, but preferably monosubstituted, preferably by $C_1$-$C_4$-alkyl, such as in particular methyl, ethyl and isopropyl, $C_3$-$C_6$-cycloalkyl, such as in particular cyclopropyl, $C_1$-$C_4$-alkoxy, such as in particular methoxy and ethoxy, $C_1$-$C_3$-hydroxyalkyl, such as in particular hydroxymethyl or hydroxyethyl, halogen, such as in particular chlorine and fluorine, hydroxy, carboxyl and cyano, $C_1$-$C_6$-alkoxycarbonyl, such as in particular methoxycarbonyl and ethoxycarbonyl, oxo and hydroximino, carbamoyl and sulphamoyl, amino, $C_1$-$C_4$-alkylamino, such as in particular methylamino and ethylamino, and $C_1$-$C_4$-dialkylamino, such as in particular diethylamino) and B denotes an alkoxy group $OR^3$, which is preferably in the "syn" position to the carboxamide group, in which $R^3$ represents $C_1$-$C_5$-alkyl, in particular methyl, or a $-(CH_2)_n(Z)_m R^4$ radical in the "syn" position in which n, m and $R^4$ have the abovementioned meaning, $-(CH_2)_n(Z)_m R^4$ preferably being $CH_2CO_2H$, $CH_2CO_2CH_3$, $CH_2CO_2C_2H_5$, $CH_2CONH_2$, $CH_2CN$, $CH(CH_3)CO_2H$, $C(CH_3)_2CO_2H$

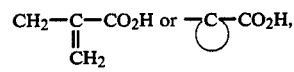

wherein

represents a carbocylic ring with 3–6 Catoms, which is optionally substituted by alkyl groups or halogen, such as chlorine or fluorine. Furthermore B preferably denotes a substituent

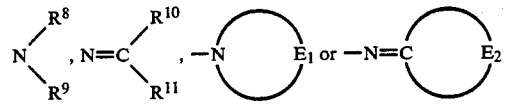

which is preferably in the syn-position to the carboxamide group and in which

preferably denotes $-(CO)-(NR^{12})-(CH_2)_n-$, $-(CS)-(NR^{12})-(CH_2)_n-$, $-(CH_2)_m-R^{13}-(CH_2)_m-$, $-(CO)_m-(CH_2)_p-$, $-(CO)_{2-m}-(CH_2)_n-(CO)_m$, $-CO-CH=CH-CO-$, $-CO-O-(CH_2)_q-$, $-CO-S-(CH_2)_q-$, $-CO-NR^{12}-CO(CH_2)_m-$, $-SO_2-(CH_2)_p-$, $-CO-(CH_2)_q-SO_2-$, $-CO-NR^{12}-N=CH-$, $-(CH=CH)_2-$, $-CO-NH-N=CH-CO-$ or $CO-(CH=CH)_2$ wherein $R^{12}$ can either have the same meaning as $R^8$ or denote

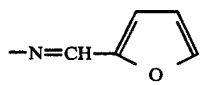

or —NHR[8]

R[13] represents O, S, SO, SO₂ or NR[14],
in which
R[14] denotes hydrogen, methyl, ethyl, cyclopropyl, methylsulphonyl or furylideneamino and
m is 1 or 2,
n is 2 or 3,
p is 3, 4 or 5 and
7 is 2, 3 or 4,
E₂ preferably represents an organic radical which forms a 4-membered to 7-membered carbocylic or heterocyclic ring with the carbon atom, the ring optionally containing 1 or 2 heteroatoms such as oxygen, sulphur or nitrogen and
R[8], R[9], R[10] and R[11] have the abovementioned meaning, but preferably represent, independently of one another, C₁–C₄-alkyl, benzyl, phenylethyl, cyclohexyl or phenyl or a heterocyclic radical such as

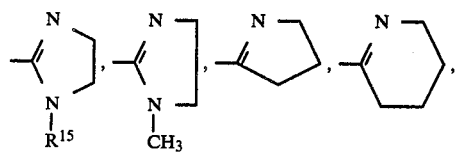

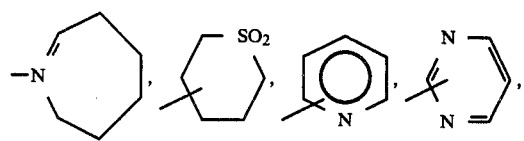

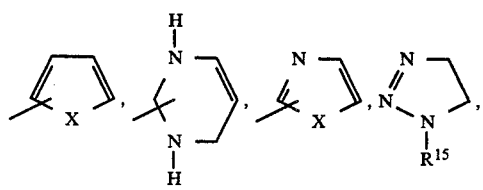

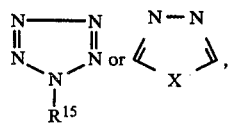

wherein
R[15] represents hydrogen or C₁–C₄-alkyl, hydroxyethyl or C₁–C₄-alkoxyethyl and
X represents S, O, SO or SO₂.

As examples of preferred compounds of the present invention there may be mentioned:

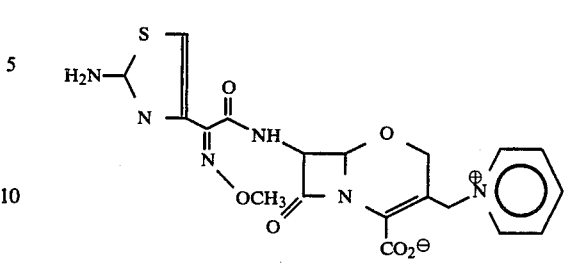

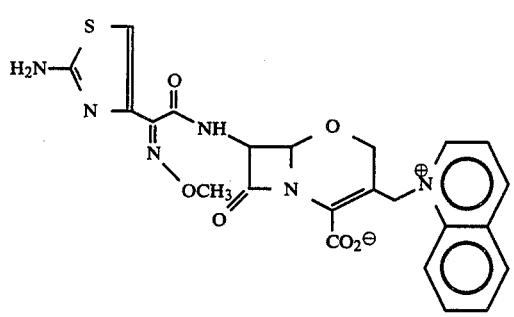

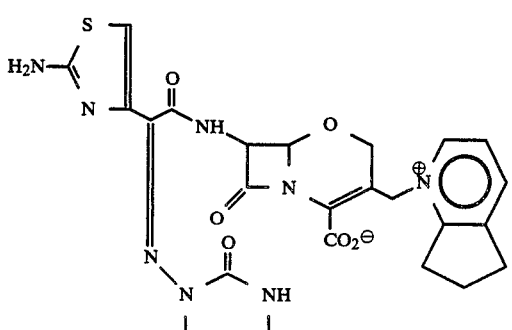

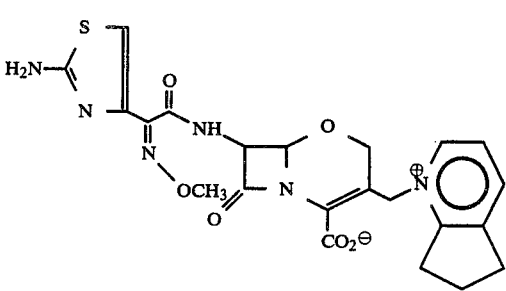

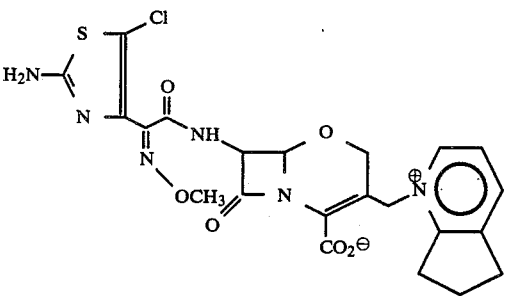

-continued

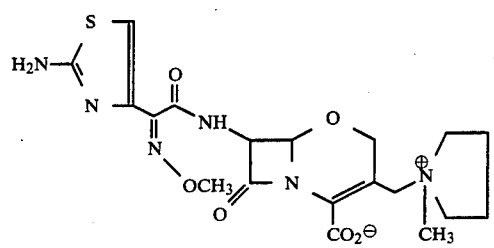

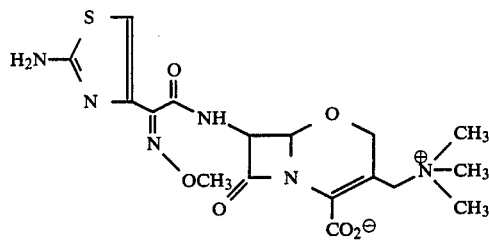

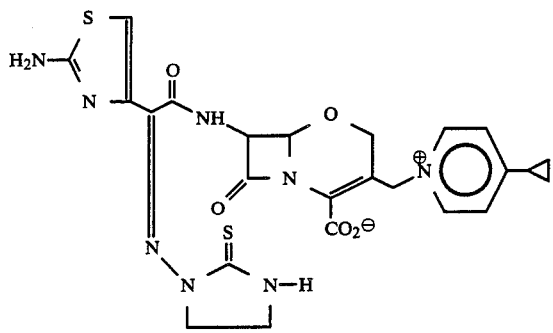

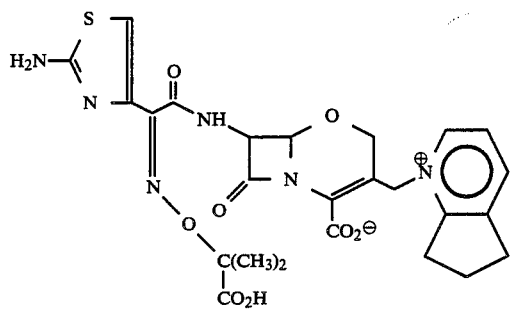

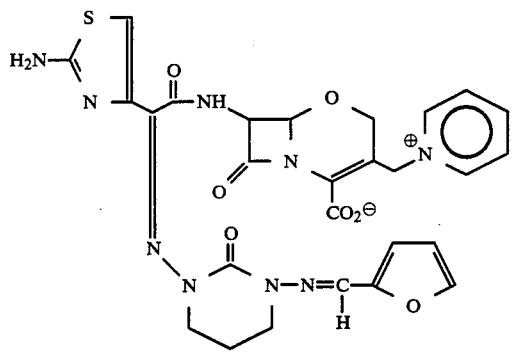

-continued

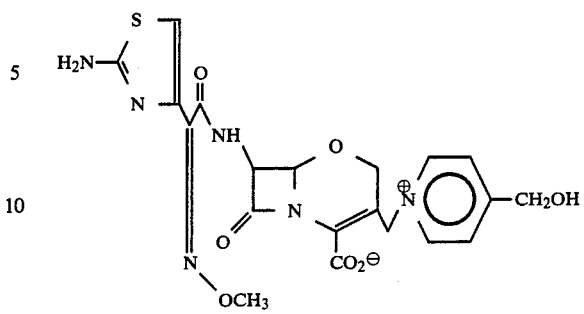

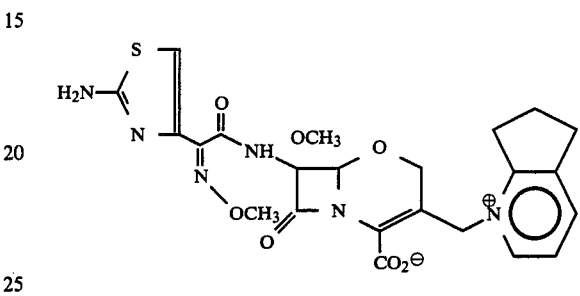

The compounds of the general formula (1) can be obtained by a process wherein (a) Compounds of the general formula (2)

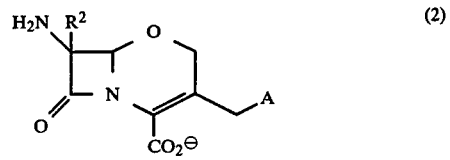

in which A and $R^2$ have the abovementioned meaning and the amino group can also be present in the form of a reactive derivative, are reacted with a 2-(2-aminothiazol-4-yl)-2-syn-oximinoacetic acid of the general formula (3)

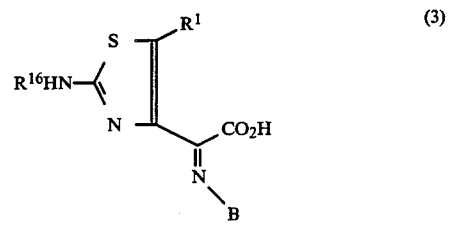

in which

B and $R^1$ have the abovementioned meaning and $R^{16}$ represents hydrogen or an amino-protective group in the form of an activated derivative of this compound, and a protective group which may be present is split off or (b) a compound of the general formula (4)

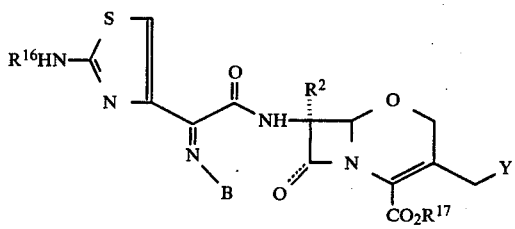

(4)

in which $R^1$, $R^2$, $R^{16}$ and B have the abovementioned meaning, $R^{17}$ denotes hydrogen or an organic ammonium radical and Y denotes a nucleofugic leaving group, preferably chlorine, bromine or iodine, chloroacetoxy, dichloroacetoxy, mesyloxy or tosyloxy, is reacted with pyridine or a pyridinium derivative which corresponds to a pyridinium radical A mentioned in formula 1, after which, if the radical $R^{16}$ is an easily removable protective group, this group is removed hydrolytically or hydrogenolytically.

The compounds of the general formula (4) can be obtained by a process wherein, in compounds of the general formula (5)

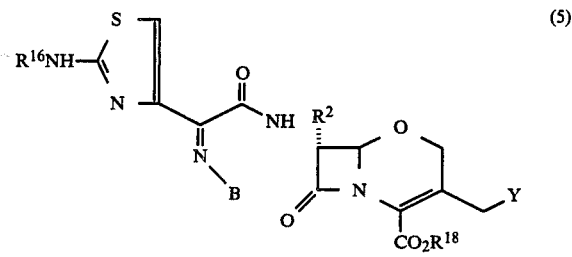

(5)

in which $R^1$, $R^2$, $R^{16}$, B and Y have the abovementioned meaning and $R^{18}$ is an easily removable carboxyl-protective group, such as, for example, tert.-butyl, benzhydryl or p-nitrobenzyl, the acid-protective group $R^{18}$ is removed analogously to known processes.

Preferably this is done, in the case of the benzhydryl ester or tert.-butyl ester, by treatment with trifluoroacetic acid in an inert organic diluent.

The componds of the general formula (5) can be obtained by reacting compounds of the general formula (3) or an activated derivative of such a compound with compounds of the general formula (6)

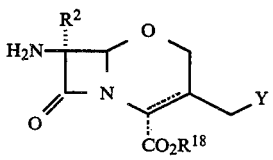

(6)

in which $R^2$, $R^{18}$ and Y have the abovementioned meaning in accordance with the methods customary in β-lactam chemistry.

The compounds of the general formula (6) with Y=Cl and OAc are already known (German Offenlegungsschrift 2,806,457 and U.S. Pat. No. 4,342,685).

The compounds of the general formula (6) with Y=-chloroacetoxy, dichloroacetoxy, mesyloxy or tosyloxy can be prepared analogously to the processes described in the literature supplied above by reacting the 3-hydroxymethyl-1-oxadethiacephamcarboxylic acid ester, formed in the course of the synthesis sequence, with chloroacetyl chloride, dichloroacetyl chloride, mesyl chloride or tosyl chloride.

If the preparation of the compounds of the general formula (1) is to be carried out by acylating compounds of the general formula (2) with compounds of the general formula (3), then suitable compounds of the general formula (3) are those in which $R^{16}$ represents hydrogen or an easily removable amino-protective group, such as, for example, a BOC-(tert.-butoxycarbonyl), Cbz-(carbobenzoxy), trit-(trityl), formyl or chloroacetyl radical.

The acylation of the compounds of the general formula (2) or (6) or, in the case of (2), of the addition salts thereof, for example the addition salts with hydrochloric acid, hydrobromic acid, nitric acid, phosphoric acid or an organic acid, such as, for example, methanesulphonic acid or p-toluenesulphonic acid, can be carried out with carboxylic acids of the general formula (3) or with a reactive derivative of such an acid. In some cases it is advantageous to protect the 2-amino group in the compounds of the general formula (3) with the abovementioned amino-protective groups $R^{16}$ prior to the reaction.

The protective group can be removed, after the acylation, in a manner known per se, for example the trityl group or BOC group by means of a carboxylic acid, such as, for example, acetic acid, trifluoroacetic acid or formic acid.

If the carboxylic acids of the general formula (3) and the derivatives thereof, protected at the amino group, are preferably themselves employed as the acylating agent, the reaction is advantageously carried out in the presence of a condensation agent, for example a carbodiimide, such as, for example, N,N'-dicyclohexylcarbodiimide.

The activation of the carboxylic acid of the general formula (3) can also be effected by treatment with certain carboxylic acid amides and, for example, phosgene, phosphorus pentachloride, tosyl chloride, thionyl chloride or oxalyl chloride.

Suitable activated derivatives of the carboxylic acids of the general formula (3) also in particular include halides, preferably chlorides, which are obtained in a manner known per se by treatment with halogenating agents, such as, for example, phosphorus pentachloride, phosgene or thionyl chloride under the gentle reaction conditions known for cephalosporin chemistry from the literature.

Further suitable activated derivatives of the carboxylic acids of the general formula (3) are the anhydrides and mixed anhydrides, azides and activated estes, preferably with p-nitrophenol, 2,4-dinitrophenol, methylenecyanohydrin, N-hydroxysuccinimide and N-hydroxyphthalimide, but preferably those with 1-hydroxybenzotriazole and 6-chloro-1-hydroxybenzotriazole. Particularly preferred mixed anhydrides are those with lower alkanoic acids such as, for example, acetic acid, and particularly preferentially those with substituted acetic acids, such as, for example, trichloroacetic acid, pivalic acid or cyanoacetic acid. However, further suitable mixed anhydrides are those with carbonic acid half-esters which are obtained, for example, by reacting the carbonic acids of the formula (3), in which the amino group is protected, with benzyl, p-nitrobenzyl, isobutyl, ethyl or allyl chloroformate. The activated derivatives can be reacted as isolated substances but can also be reacted in situ.

If, in the compounds of the general formula (2) or (6), the amino group is present in the form of a reactive derivative, then this can be a derivative of the type known from the literature for amidation reactions. Thus, for example, it is possible to use silyl derivatives which are formed on reacting compounds of the general formula (2) or (6) with a silyl compound, such as, for example, trimethylchlorosilane or bis-(trimethylsilyl)-acetamide. If the reaction is carried out with such a compound activated at the amino group, it is advantageously performed in an inert solvent, such as, for example, methylene chloride, tetrahydrofuran or dimethylformamide. If the compounds of the general formula (2) are employed, an excess of bis-(trimethylsilyl)-acetamide (5-10 mole equivalents) is preferably used, whereby the carboxyl group is also silylated and as a result the solubilities of the compounds of the general formula (2) in the abovementioned solvents are improved.

In general, the reaction of the 1-oxadethiacephems of the general formula (2) or (6) with a carboxylic acid of the general formula (3) or an activated derivative thereof is carried out in the presence of an inert solvent. In particular, suitable solvents are chlorinated hydrocarbons, such as, preferably, methylene chloride and chloroform; ethers, such as for example diethyl ether and preferably tetrahydrofuran and dioxane; ketones, such as preferably acetone and butanone; amides, such as preferably dimethylformamide and dimethylacetamide or water. It can also prove advantageous to use mixtures of the said solvents. This is often the case if the 1-oxadethiacephem compounds of the general formula (2) or (6) are reacted with an activated derivative, produced in situ, of a carboxylic acid of the formula (3).

The reaction of compounds of the formula (2) or (6) with carboxylic acids of the formula (3) or their activated derivatives can be carried out in a temperature range from about $-80°$ to about $+80°$ C., preferably between $-30°$ and $+50°$ C., but especially between about $-20°$ C. and room temperature.

The reaction time depends on the reactants, the temperature and the solvent mixture and is normally between about half an hour and about 30 hours.

The reaction with acid halides can, if appropriate, be carried out in the presence of an acid-binding agent to bond the hydrogen halide liberated. Suitable agents are in particular tertiary amines, such as, for example, triethylamine or dimethylaniline, inorganic bases, such as, for example, potassium carbonate or sodium carbonate, and alkylene oxides, such as, for example, propylene oxide. The presence of a catalyst, such as, for example, dimethylaminopyridine, can at times also be of advantage.

If the compounds of the general formula (1) are to be prepared by nucleophilic replacement of Y, in the compounds of the general formula (4), by pyridine or one of the stated pyridine derivatives, suitable radicals Y are halogen atoms, preferably chlorine, but also chloroacetoxy, dichloroacetoxy, mesyloxy or tosyloxy. $R^{17}$ is preferably hydrogen.

The pyridine component is added in amounts between the equimolar amount and an up to 30-fold excess.

Suitable solvents for these reactions are all inert organic diluents. These include halogenated hydrocarbons, such as methylene chloride, chloroform, 1,2-dichloroethane, cyclic ethers, such as tetrahydrofuran and dioxane, or dipolar aprotic solvents such as, for example, dimethylformamide or mixtures thereof.

The reactions are in general carried out at temperatures between $-20°$ C. and $40°$ C., preferably at $0°$ C. to $25°$ C.

In the reactions of the compounds of the general formula (5) to give the compounds of the general formula (4), it is possible to use all reagents capable of selectively cleaving the acid-protective groups conventionally employed in $\beta$-lactam chemistry. These preferably include formic acid and anhydrous trifluoroacetic acid. The reaction can, if appropriate, be carried out in the presence of 1 to 10 equivalents of amisole.

Suitable diluents are all inert organic solvents, such as, for example, halogenated hydrocarbons, such as methylene chloride, chloroform, carbon tetrachloride or 1,2-dichloromethane.

The reactions are in general carried out at temperatures of between $-70°$ C. and $40°$ C., preferably between $-10°$ C. and $0°$ C.

When stripping off the solvent after the reaction (5)→(4) has taken place, it is advisable to add 1-50 mole equivalents of an aromatic hydrocarbon, preferably benzene.

The compounds of the general formula (4) can be isolated as such, but are preferably reacted directly after distilling off the solvent and the excess acid, as described above, to give compounds of the general formula (1).

If 2-(2-aminothiazol-4-yl)-2-syn-methoximino-acetic acid and (6R,7S)-7$\beta$-amino-3-[(2,3-cyclopenteno-1-pyridino)methyl-8-oxo-5-oxa-1-aza-bicyclo[4.2.0]oct-2-ene-2-carboxylate are used as starting materials, the course of the reaction can be represented by the formula diagram I:

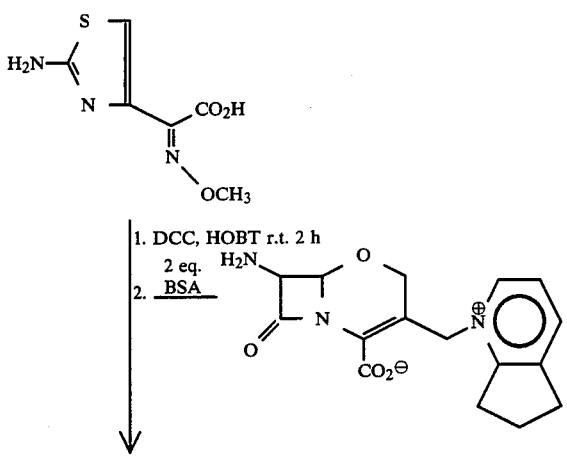

-continued
Diagram I

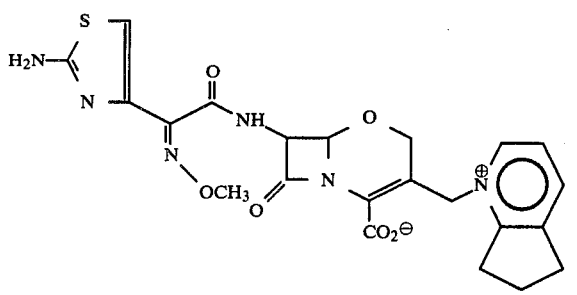

r.t.: room temperature
DCC: N,N—dicyclohexylcarbodiimide
HOBT: 1-hydroxy-1H—benzotriazole
BSA: bis-(trimethylsilyl)-acetamide If (6R, 7S)-7β-amino-3-chloromethyl-8-oxo-5-oxa-1-aza-bicyclo[4.2.0]oct-2-ene-2-carboxylic acid benzhydryl ester and 2-(2-aminothiazol-4-yl)-2-syn-methoxyiminoacetic acid and pyridine are used as starting materials, the course of the reaction can be represented by the formula diagram II:

Diagram II

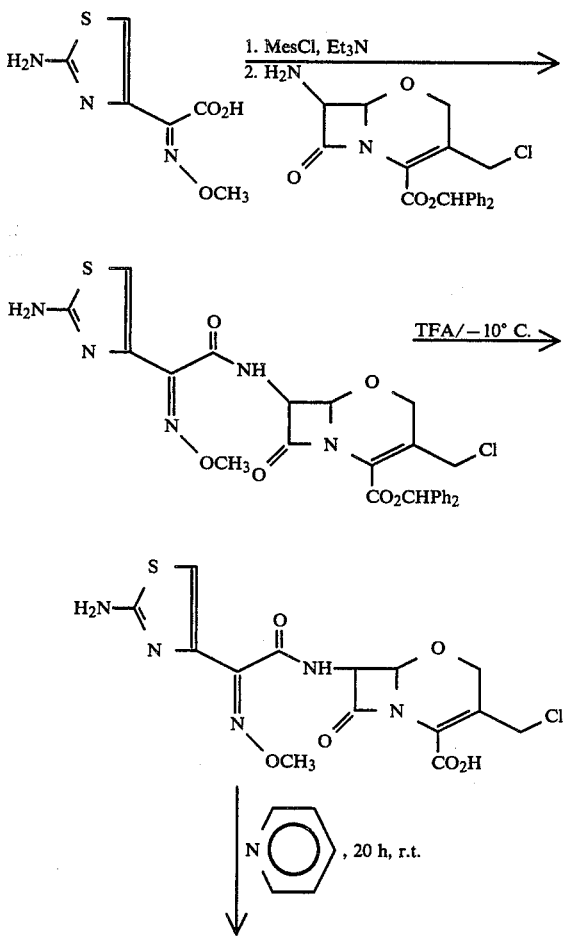

-continued
Diagram II

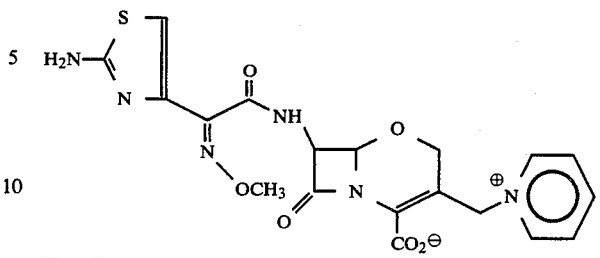

TFA: trifluoroaceticanhydride

The compounds according to the invention exhibit a powerful and broad antimicrobial activity, especially against gram-negative and gram-positive bacteria. These properties permit their use as chemotherapeutic active substances in medicine. With the aid of these compounds, the diseases caused by gram-negative and gram-positive bacteria and bacteria-like microorganisms can be prevented, ameliorated and/or cured.

The compounds according to the invention are particularly active against bacteria and bacteria-like microorganisms.

They are therefore particularly suitable for the prophylaxis and chemotherapy of local and systemic infections, caused by these pathogens, in human and veterinary medicine.

For example, it is possible to treat and/or prevent local and/or systemic diseases caused by the following pathogens or mixtures of the following pathogens: pseudomonoadaceae, such as Pseudomonas bacteria, for example *pseudomonas aeruginosa* (PS=pseudomonas); micrococcaceae, such as staphylococci, for example *Staphylococcus aureus, Staph. emidermidis, Staph. aerogenes* and *Gaffkya tetragena* (Staph.=Staphylococcus): lactobacteriaceae, such as streptococci, for example *Streptococcus pyogenes*, α- and β-haemolysing streptococci, non (γ)-haemolysing streptococci, *Str. viridans, Str. faecalis* (enterococci) and *Dipolococcus pneumoniae* (pneumococci) (Str.=Streptococcus); enterobacteriaceae, such as *Escherichiae bacteria* of the coli group; Escherichia bacteria, for example *Escherichia coli*, Enterobacter bacteria, for example E-aerogenes and *E. cloacae*, *Klebsiella bacteria*, for example *K. pneumoniae*, Serratia, for example Serratia marvescens (E.=Enterobacter) (K.=Klebsiella), Proteae bacteria of the Proteus group; Proteus, for example *Proteus vulgaris, Pr. morganii, Pr. rettgeri* and *Pr. mirabillis* (Pr.=Proteus); and bacteroidaceae, such as Bacteroides bacteria, for example *Bacteroides fragilis* (B.=Bacteroides).

The above recital of pathogens is purely by way of example and is in no way to be interpreted as implying a limitation.

As examples of diseases which can be prevented, ameliorated and/or cured by the compounds according to the invention there may be mentioned: diseases of the respiratory tracts and of the throat; otitis; pharyngitis; pneumonia; peritonitis; pyelonephritis; cystitis; endocarditis; systemic infections; bronchitis; arthritis; local infections.

The present invention also includes pharmaceutical preparations which in addition to non-toxic, inert pharmaceutically suitable excipients contain one or more of the compounds according to the invention, or which consist of one or more active substances according to the invention.

The present invention also includes pharmaceutical preparations in dosage units. This means that the preparation is in the form of individual parts, for example tablets, dragees, capsules, pills, suppositories and ampules, the active substance content of which corresponds to a fraction or a multiple of a single dose. The dosage units may for example contain 1, 2, 3 or 4 individual doses or ½, ⅓ or ¼ of an individual dose. An individual dose preferably contains the amount of active substance which is given in only one administration and which usually corresponds to the whole, one half or one third or one quarter of a daily dose.

By non-toxic, inert pharmaceutically suitable excipients there are to be understood solid, semi-solid or liquid diluents, fillers and formulation auxiliaries of all kinds.

As preferred pharmaceutical preparations there may be mentioned tablets, dragees, capsules, pills, granules, suppositories, solutions, suspensions, emulsions, pastes, ointments, gels, creams, lotions, powders and sprays.

Tablets, dragees, capsules, pills and granules may contain the active substance or substances alongside conventional excipients, such as (a) fillers and extenders, for example, starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin and (f) absorption accelerators, for example quaternary ammonium compounds, (g) wetting agents, for example cetyl alcohol and glycerol monostearate, (h) adsorbents, for example kaolin and bentonite and (i) lubricants, for example talc, calcium/-magnesium stearate and solid polyethylene glycols, or mixtures of the substances listed under (a) to (i).

The tablets, dragees, capsules, pills and granules can be provided with the conventional coatings and shells, optionally containing opacifying agents, and can also be of such composition that they release the active substance or substances only, or preferentially, in a particular part of the intestinal tract, optionally in a delayed manner, possible embedding compositions being, for example, polymeric substances and waxes.

The active substance or substances can optionally also be present in micro-encapsulated form together with one or more of the abovementioned carriers.

Suppositories may contain, in addition to the active substance or substances, the customary water-soluble or water-insoluble carriers, for example polyethylene glycols, fats, for example obtained from a $C_{14}$-alcohol and $C_{16}$-fatty acid) or mixtures of these substances.

For parenteral administration, the solutions may also be present in a sterile form, isotonic with blood.

The therapeutically active compounds should preferably be present in the abovementioned pharmaceutical preparations in a concentration of about 0.1 to 99.5, preferably from about 0.5 to 95, % by weight of the total mixture.

The abovementioned pharmaceutical preparations may in addition to the compounds according to the invention also contain other pharmaceutically active substances.

The abovementioned pharmaceutical preparations are produced in a conventional manner by known methods, for example by mixing the active substance or substances with the carrier or carriers.

The active substances or the pharmaceutical preparations can be administered locally, orally, parenterally, intraperitoneally and/or rectally, preferably orally or parenterally, such as intravenously or intramuscularly.

In general it has proved advantageous, both in human and veterinary medicine, in order to achieve the desired results, to administer the active substance or substances according to the invention in total amounts of about 1 to about 1000, preferably 1 to 200, mg/kg of body weight per 24 hours, if appropriate in the form of several individual administrations. An individual administration preferably contains the active substance or substances according to the invention in amounts of about 1 to about 250, especially 1 to 60, mg/kg of body weight. It can however be necessary to deviate from the dosages mentioned and in particular to do so as a function of the species and body weight of the subject to be treated, the nature and severity of the diseases, the nature of the preparation and administration of the medicament and the period or interval over which it is administered. Thus it can in some cases suffice to manage with less than the abovementioned amount of active substance while in other cases the abovementioned amount of active substance has to be exceeded. The optimum dosage and type of administration of the active substances, required in each particular case, can easily be laid down by any expert on the basis of his expert knowledge.

In order to broaden the spectrum of action, the compounds according to the invention can be combined with another β-Lactam antibiotic or with aminoglycoside antibiotics, such as, for example, gentamicin, sisomicin, kanamicin, amikacin or tobramicin.

The compounds according to the invention are particularly suitable for use in combating infectious diseases, especially in combating bacterial infections.

MIC TABLE

| Germs | Iso-Sensitest agar Germ dilution. Overnight culture 1:500 Concentration of preparations: μg/ml | | | | |
|---|---|---|---|---|---|
| | Example 1 | Example 2 | Example 3 | Mezlocillin | Cefofaxim |
| E. coli T 7 | 4 | 4 | 2 | >128 | ≦0.062 |
| E. coli A 261 | ≦0.062 | 0.125 | ≦0.062 | 128 | ≦0.062 |
| E. coli Neumann | ≦0.062 | ≦0.062 | ≦0.062 | 0.25 | ≦0.062 |
| E. coli 183/58 | ≦0.062 | 0.25 | ≦0.062 | 4 | 0.5 |
| E. coli F 14 | 16 | 32 | 8 | >128 | <0.062 |
| E. coli C 165 | ≦0.062 | ≦0.062 | ≦0.062 | 1 | ≦0.062 |
| E. coli 4322 | ≦0.062 | 1 | ≦0.062 | 2 | ≦0.062 |
| Klebs. 57 USA | 0.5 | 2 | 0.5 | >128 | ≦0.062 |
| Klebs. 63 | ≦0.062 | 0.125 | ≦0.062 | 2–4 | ≦0.062 |
| Klebs. 1852 | 1 | 2 | 0.5 | >128 | ≦0.062 |
| Klebs. 6097 | ≦0.062 | 0.25 | ≦0.062 | 8 | ≦0.062 |
| Serratia 16001 | ≦0.062 | 0.125 | 0.5 | 2 | 0.5 |
| Serratia 16002 | 1 | 0.25 | 0.5 | 4 | 0.25 |

MIC TABLE-continued

Iso-Sensitest agar
Germ dilution. Overnight culture 1:500
Concentration of preparations: μg/ml

| Germs | Example 1 | Example 2 | Example 3 | Mezlocillin | Cefofaxim |
|---|---|---|---|---|---|
| Provid. 12012 | ≦0.062 | 0.025 | ≦0.062 | 2 | ≦0.062 |
| *Prot. mag.* 932 | 1 | 4 | 0.125 | 32 | 4 |
| *Prot. vulg.* 9023 | 0.25 | 0.25 | ≦0.062 | 1 | ≦0.062 |
| *Prot. vulg.* 1017 | 32 | 32 | 16 | 4 | 0.25 |
| *Prot. vulg.* N 6 | 0.25 | 0.25 | 0.125 | 0.5 | ≦0.062 |
| *Prot. rettg.* 10007 | ≦0.062 | ≦0.062 | ≦0.062 | 0.05 | ≦0.062 |
| *Prot. mirab.* 1235 | 0.125 | 0.125 | ≦0.062 | 0.125 | ≦0.062 |
| Staph. 1756 | >128 | >128 | >128 | 64 | >128 |
| Staph. 133 | 0.25 | 0.5 | 0.125 | 0.5 | 1 |
| Staph. 25022 | 0.5 | 1 | 0.25 | 1-2 | 1 |
| Staph. 25470 | >128 | >128 | >128 | 32-64 | >128 |
| Staph. E 25185 | 0.125 | 0.25 | ≦0.062 | 1 | 0.5 |
| *Strept. faec.* 27101 | >128 | >128 | >128 | 64 | >128 |
| *Strept. faec.* 113 | 8 | 32-64 | 16 | 1 | 128 |
| Enterocoe 9790 | >128 | >128 | >128 | 2 | >128 |
| Enterocoe 27158 | 128 | 16 | 128 | 2 | 64 |
| Pseudom. F 41 | 1 | 4 | 0.5 | 32 | 16 |
| Pseudom. Walter | 2 | 2 | 1 | 32 | 16 |
| Pseudom. 7035 | 2 | 2 | 1-2 | 16 | 16 |
| Pseudom. 7451 | 2 | 16 | 4 | 64 | 64 |
| *Enterob. cloacae* 56US | >128 | 128 | 64 | 64 | >128 |
| *Enterob. cloacae* 5744 | 0.5-2 | 0.5 | ≦0.062 | 16 | 0.125 |
| Achromob. CB 20005 | 0.25 | 0.5 | ≦0.062 | 2 | ≦0.062 |

EXAMPLE 1

(6R,7S)-7-[2-(2-Aminothiazol-4-yl)-2-syn-methoxyiminoacetamido]-3-[1-pyridinomethyl]-8-oxo-5-oxa-1-aza-bicyclo-[4.2.0]oct-2-ene-2-carboxylate (a) 0.24 g of N-hydroxybenztriazole is added, at room temperature, to a solution of 0.36 g of 2-(2-aminothiazol-4-yl)-2-syn-methoximinoacetic acid in 5 ml of absolute DMF, the mixture is cooled to 10° C. and a solution of 0.37 g of N,N-dicyclohexylcarbodiimide in 2 ml of absolute DMF is added. The batch is stirred for 2 hours at room temperature and a solution of 0.7 g of (6R, 7S)-7-amino-3[1-pyridinomethyl]-8-oxo-5-oxa-1-aza-bicyclo[4.2.0]oct-2-ene-2-carboxylate (2a) and 0.73 g of bis-(trimethylsilyl)-acetamide in 3 ml of absolute DMF, precooled to −10° C. is added. This batch is stirred for 4 hours at room temperature, 200 ml of acetone are added and the precipitate which forms is filtered off with suction. 310 mg of the crude compound shown in the title are obtained and are chromatographed on silica gel, using a 2/1 acetonitrile/water mixture. Evaporation of the acetonitrile and freeze drying gives 61 mg of the pure compound shown in the title as a colorless lyophilizate.

Rf: (CH$_3$CN/H$_2$O=2/1)=0.27

$^1$H-NMR (200 MHz, D$_2$O): δ=3.85 (s; 3H, OCH$_3$) 4.27 and 4.39 (AB system, J$_{AB}$=18.5 Hz; 2H, OCH$_2$) 5.23 (d, J=4 Hz; 2H, 6-H); 5.49 (d, J=4 Hz; 1H, 7-H); 5.19 and 5.64 (AB system, J$_{AB}$=15 Hz; 2H CH$_2$—N⊕); 6.87 (s; 1H, thiazole-H) 7.95 (t, J=7.5H$_2$; 2H, 2,5-pyrid-H); 8.70 (t, J=7.5 Hz; 1H, 4-pyrid-H); 8.86 (d, J=6 Hz; 2H, 2,6-pyrid-H).

(b) A solution of 0.53 g of 2(-2-aminothiazol-4-yl)-2-syn-methoximinoacetic acid (3a) and 1.38 ml of triethylamine in 5 ml of absolute DMF is cooled to −50° C. under N$_2$ and 0.21 ml of mesyl chloride is added. The mixture is briefly warmed to −25° C., so that a clear solution forms, and is then cooled to −50° C. again and stirred for 30 minutes (solution 1).

In a separate flask, 0.3 ml of triethylamine is added, with ice cooling, to 0.86 g of (6R,7S)-7-amino-3[1-pyridinomethyl]-8-oxo-5-oxa-1-aza-bicyclo[4.2.0]oct-2-ene-carboxylate dissolved in 1 ml of water. Solution 1 is added to the solution thus obtained, with ice cooling, and while keeping the pH at 8–9 by gradual addition of triethylamine. Stirring is continued for 30 minutes, 200 ml of acetone are added and the product is filtered off with suction. After chromatography (silica gel; CH$_3$CN/H$_2$O=2) and freeze drying, 20 mg of the compound shown in the title are obtained as a colorless lyophilizate. [Physical data identical with Example 1a)].

EXAMPLE 2

(6R,7S)-7-[2-(2-Aminothiazol-4-yl)-2-syn-ethoxyiminoacetamido]-3-[1-pyridinomethyl]-8-oxo-5-oxa-1-aza-bicyclo[4.2.0]-oct-2-ene-2-carboxylate The procedure followed was analogous to that described in Example 1a). 1.3 g (2a) and 0.72 g of 2(-2-aminothiazol-4-yl)-2-syn-ethoxyiminoacetic acid (3b) were used.

41 mg of the compound shown in the title were obtained as a colorless lyophilizate of Rf=0.28.

$^1$H-NMR (D$_2$O, 200 MHz): δ=1.23 (t, J=7.5 Hz; 3H, CH$_3$); 4.24 (q, J=7.5 Hz; 2H, CH$_2$—CH$_3$); 4.40 and 4.55 (AB-system, J$_{AB}$=18.5 Hz; 2H, O—CH$_2$); 5.43 (d, J=4 Hz; 1H, 6-H); 5.63 (d, J=4 Hz;⊕1H, 7-H); 5.34 and 5.79 (AB-system, J$_{AB}$=15 Hz; 2H, CH$_2$N); 6.97(s; 1H, thiazole-H); 8.12 (t, J=7.5 Hz; 2H, 3,5-pyrid-H); 8.62 (t; J=7.5 Hz; 1H, 4-pyrid-H); 9.03 (d, J=7 Hz; 2H, 2,6-pyrid-H).

EXAMPLE 3

(6R,7S)-7-[2-(2-Aminothiazol-4-yl)-2-syn-methoximinoacetamido]-3-[(2,3-cyclopenteno-1-pyridino)-methyl]-8-oxo-5-oxa-1-aza-bicyclo[4.2.0]oct-2-ene-2-carboxylate The procedure followed was as described in Example 1a). 0.36 g of (6R,7S)-7-amino-3[(2,3-cyclopenteno-1-pyridino)-methyl]-8-oxo-5-oxa-1-aza-bicyclo[4.2.0]oct-2-ene-2-carboxylate and 0.16 g of (3a) were employed. 37 mg of the compound shown in the title were obtained as a colorless lyophilizate, with Rf=0.29 ($CH_3CN/H_2O$=2/1).

$^1$H-NMR (200 MHz, $D_2O$) δ=2.19 (heptuplet recognized as t, J=7.5 Hz; 2H, β-cyclopent.-H), 3.07 (t, J=8 Hz; 2H,γ-cyclopent.-H); 3.84 (s; 1H, $OCH_3$); 4.2 and 4.34 (AB-system, $J_{AB}$=18.5 Hz; 2H, O—$CH_2$); 5.18 (d, J=4 Hz;⊕1H, 6-H); 5.27 and 5.37 (AB-system, $J_{AB}$=16 Hz; 2H, $CH_2$—N); 5.49 (d, J=4 Hz; 1H, 7-H); 6.86 (s; 1H, thiazole-H); 7.62 (t, J=7.5 Hz; 1H, 5-pyrid.-H); 8.15 (d, J=7.5 Hz; 1H, 4-pyrid.-H); 8.44 (d, J=7.5 Hz; 1H, 6-pyrid.-H).

EXAMPLE 4

(6R,7S)-7-[2-Aminothiazol-4-yl)-2-syn-ethoximinoacetamido]-3-[(2,3-cyclopenteno-1-pyridino)-methyl]-8-oxo-5-oxa-1-aza-bicyclo[4.2.0]oct-2-ene-carboxylate The procedure followed was analogous to that of Example 1a). The compound shown in the title was obtained, with Rf=0.28 and $^1$H-NMR (200 MHz; $D_2O$): δ=1.25 (t, J=7.5 Hz; 3H, $CH_3$); 2.20 (heptuplet recognized as t, J=7.5 Hz; 2H, β-cyclopent.-H); 3.12 (t, J=8 Hz; 2H,γ-cyclopent.-H); 3.25 (t, J=8 Hz; 2H, α-cyclopent.-H); 4.28 (q, J=7.5 Hz; 2H, $CH_2$-$CH_3$); 4.29 and 4.41 (AB-system, $J_{AB}$=18.5 Hz; 2H, $OCH_2$); 5.21 (d, J=4 Hz; 1H,⊕6-H); 5.30 and 5.39 (AB-system), $J_{AB}$=16 Hz; 2H, $CH_2$-N); 5.50 (d, J=4 Hz; 1H, 7-H); 6.90 (s; 1H, thiazole-H); 7.64 (t, J=7.5 Hz; 1H, 5-pyrid.-H); 8.18 (d, J=7.5 Hz; 1H, 4-pyrid.-H); 8.49 (d, J=7.5 Hz; 1H, 6-pyrid.-H):

EXAMPLE 5

(6R,7S)-7-[2-(2-Aminothiazol-4-yl)-2-syn-methoximinoacetamido]-3-chloromethyl-8-oxo-5-oxa-1-azabicyclo[4.2.0]-oct-2-ene-2-carboxylic acid benzhydryl ester 0.7 ml of mesyl chloride was added to a solution of 1.82 g of (3a) and 2.2 ml of triethylamine in 10 ml of DMF at −50° C., under a $N_2$ atmosphere, and the mixture was then stirred for 30 minutes at −50° C. and 20 minutes at −25° C. Thereafter a solution of 3 g of (6R,7S)-7-amino-3-chloromethyl-8-oxo-5-oxa-1-azabicyclo[4.2.0]oct-2-ene-2-carboxylic acid benzylhydryl ester dissolved in 2 ml of THF and precooled to −40° C. was added and the batch was stirred at −40° C. It was allowed to come to room temperature, 200 ml of phosphate buffer solution (pH=7) were added and the whole was extracted three times with 100 ml of ethyl acetate at a time. The combined organic extracts were washed with saturated $NaHCO_3$ solution and with water, and were dried over $MgSO_4$, and the solvent was stripped off in vacuo. 3.3 g of the crude compound shown in the title were obtained, and were chromatographed on silica gel, using a 1/1 toluene/ethyl acetate mixture, followed by ethyl acetate. 350 mg of the pure compound shown in the title were obtained, with Rf=0.38 (ethyl acetate).

$^1$H-NMR (200 MHz, $CDCl_3$): δ=4.04 (s; 3H, $OCH_3$); 4.48 and 4.64 (AB-system, $J_{AB}$=17.5 Hz; 2H, $OCH_2$); 4.58 and 4.59 (2a; 2H, $CH_2Cl$); 5.19 (d, J=4 Hz; 1H, 6-H); 5.88 (dd, $J_1$=4 Hz, $J_2$=10 Hz; 1H, 7-H); 6.90 (s; 1H; $CH(Ph)_2$); 6.94 (S; 1H, thiazole-H); 7.15–7.55 (m; 11H, phenyl and NH).

EXAMPLE 6

(6R,7S)-7-[2-(2-Aminothiazol-4-yl)-2-syn-methoximinoacetamido]-3-[(2,3-cyclopenteno-1-pyridino)-methyl]-8-oxo-5-oxa-1-aza-bicyclo[4.2.0]oct-2-ene-2-carboxylate 1.42 ml of trifluoroacetic acid were added, under a nitrogen atmosphere, to a solution, cooled to −10° C., of 280 mg of the title compound from Example 5 in 3 ml of absolute dichloroethane and 1 ml of anisole. The mixture was stirred for 30 minutes at −10° C., 5 ml of benzene were added and the batch was concentrated in vacuo (bath temperature 15° C.) to one-quarter of its volume. It was then diluted with 2 ml of absolute THF and cooled to −15° C., and 2 ml of 2,3-cyclopentenopyridine were added. The mixture was allowed to come to room temperature and was stirred for a further 20 hours. 2 ml of THF were added and 50 ml of diethyl ether were run in slowly, with stirring. The precipitate was filtered off with suction under a nitrogen atmosphere, washed with ether and chromatographed on silica gel, using a 2/1 acetonitrile/$H_2O$ mixture. Evaporation of the acetonitrile and subsequent freeze drying gave 21 mg of the compound shown in the title (identical with the product obtained according to Example 1(a)).

It will be understood that the specification and examples are illustrative but not limitative of the present invention and that other embodiments within the spirit and scope of the invention will suggest themselves to those skilled in the art.

We claim:

1. A 1-oxadethiacephalosporin derivative of the formula

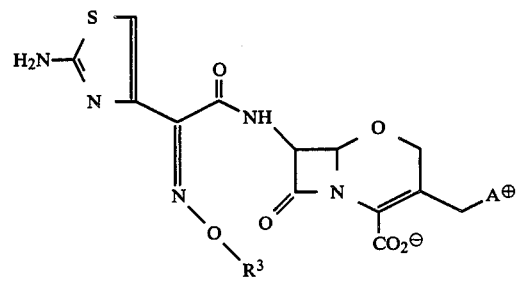

in which
$R^3$ is methyl or ethyl, and
A is pyridinium or trimethylenepyridinium.

2. A 1-oxadethiacephalosporin derivative according to claim 1, of the formula

3. A 1-oxadethiacephalosporin derivative according to claim 1, of the formula

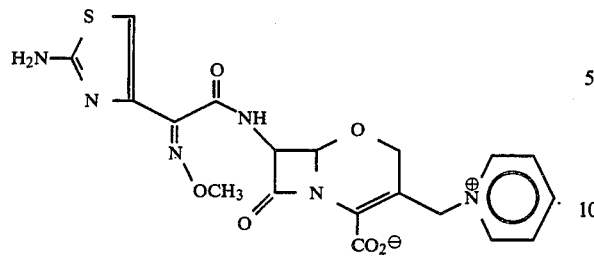

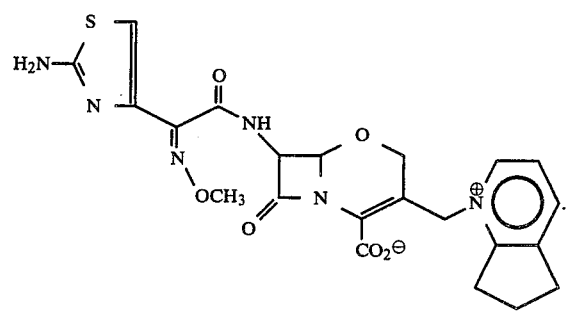

4. An antibacterial composition comprising an antibacterially effective amount of a compound according to claim 1 in admixture with a diluent.

5. A unit dose of a composition according to claim 4 in the form of a tablet, capsule or ampule.

6. A method of combating bacteria which comprises administering to a patient an antibacterially effective amount of a compound according to claim 1.

7. The method according to claim 6, wherein such compound is

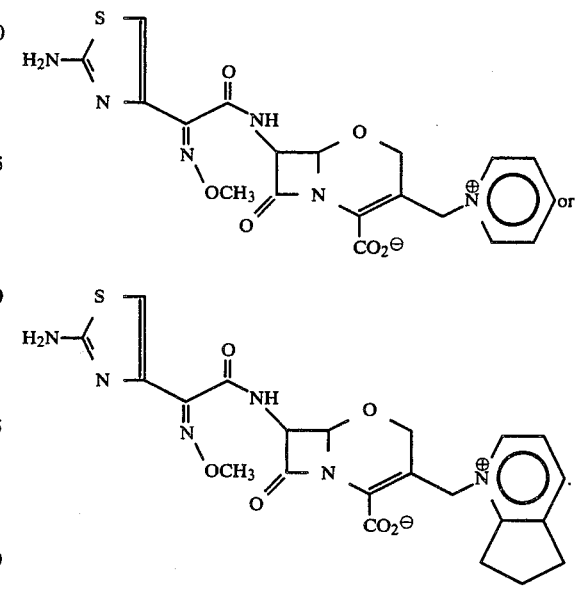

* * * * *